United States Patent [19]

Harvey et al.

[11] 4,357,313

[45] Nov. 2, 1982

[54] RHEOLOGICALLY DESIRABLE TOOTHPASTE

[75] Inventors: Kenneth Harvey, Wilmslow; Stephen T. Connors, Sale, both of England

[73] Assignee: Colgate Palmolive Company, New York, N.Y.

[21] Appl. No.: 219,297

[22] Filed: Dec. 22, 1980

[30] Foreign Application Priority Data

Dec. 19, 1979 [GB] United Kingdom ............... 7943639

[51] Int. Cl.³ .............................................. A61K 7/16
[52] U.S. Cl. ..................................... 424/49; 424/52; 424/54; 424/56; 424/57
[58] Field of Search ..................................... 424/49–58

[56] References Cited

U.S. PATENT DOCUMENTS

| | | | |
|---|---|---|---|
| 3,842,167 | 10/1974 | Block et al. | 424/49 |
| 3,864,470 | 2/1975 | Watson | 424/49 |
| 3,934,000 | 1/1976 | Barth | 424/49 |

FOREIGN PATENT DOCUMENTS

| | | |
|---|---|---|
| 1186706 | 4/1970 | United Kingdom . |
| 1372663 | 11/1974 | United Kingdom . |
| 1372941 | 11/1974 | United Kingdom . |
| 1373001 | 11/1974 | United Kingdom . |
| 1400153 | 7/1975 | United Kingdom . |
| 1400154 | 7/1975 | United Kingdom . |
| 1409289 | 10/1975 | United Kingdom . |
| 1429774 | 3/1976 | United Kingdom . |
| 1433743 | 4/1976 | United Kingdom . |

*Primary Examiner*—Shep K. Rose
*Attorney, Agent, or Firm*—Robert L. Stone; Murray M. Grill; Herbert S. Sylvester

[57] ABSTRACT

A toothpaste of improved rheological properties wherein drying and plug formation is reduced or prevented. The toothpaste contains a vehicle in which there is present about 45–85% by weight of liquid phase containing up to about 35% by weight of sorbitol and at least about 25% by weight of water and a solid phase including about 0.5–10% by weight of gelling agent. Drying and plug formation is reduced by including in the liquid phase about 5–20% by weight of polyethylene glycol having an average molecular weight between about 900 and 1600.

10 Claims, No Drawings

RHEOLOGICALLY DESIRABLE TOOTHPASTE

This invention relates to a toothpaste having desirable rheological characteristics.

A typical toothpaste vehicle is comprised of liquids such as water and humectant and solids such as gelling agents proportioned to provide a creamy or gel-like consistency. When the particular components used are unwisely chosen or their proportion to each other is improper, rheological problems can occur. Such problems include undue hardness or undue liquidity, syneresis or phase separation, drying (especially at the cap and, therefore, called "plugging") particularly should the tube be left open etc.

Sorbitol solution in water, typically about 50–80% by weight solution, most often about 70% solution, and glycerin are the most commonly used toothpaste humectants. They are generally used in amounts ranging up to about 80% by weight of a toothpaste but most often about 15–40%. Typically water is also present, possibly in amounts of up to about 80% by weight of a toothpaste, such as in amounts of about 20–60%.

When Sorbitol solution and water (separate from that in which the sorbitol is dissolved) are present in amount of up to about 35% by weight and at least about 25% by weight, respectively, after proportioning these liquids with gelling agent drying readily occurs and a hard plug forms at the cap of a toothpaste tube making it very difficult to effectively extrude the paste. Some drying may occur when glycerine is used in place of all or part of the sorbitol solution although the plug which might form would not be as hard.

It is an advantage of this invention that drying of high water content toothpastes containing sorbitol as humectant and gelling agent is reduced or prevented. Other advantages will be apparent upon consideration of the following specification.

In accordance with certain of its aspects this invention relates to a toothpaste comprising a vehicle containing about 45–85% by weight of liquid phase which contains up to about 35% by weight (based on the toothpaste) of sorbitol and at least about 25% by weight (based on the toothpaste) of water and a solid phase including about 0.5–10% by weight of gelling agent, wherein there is present as an agent of the liquid phase which reduces drying of said toothpaste about 5–20% by weight of polyethylene glycol having an average molecular weight between about 900 and 1600.

Applicants are aware that polyethylene glycol has been used in dentifrices in the past. However, when polyethylene glycol of average molecular weight between about 900 and 1600 has been suggested the dentifrice is typically of low water content or is anhydrous or does not contain sorbitol. Such prior dentifrices are indicated in U.S. Pat. Nos. 3,689,637 to Pader, 3,836,641 to Hoyles et al; and 3,864,470 to Watson and British Pat. No. 1,310,374 to Clippingdale et al.

In the toothpaste of the present invention up to about 35% by weight of sorbitol is present, typically about 15–35%, preferably about 20–25%. If desired, minor amounts (e.g. about 1–10%) of other humectants such as glycerine or polyethylene glycol of average molecular weight of about 380–420 may also be mixed with sorbitol. Glycerine can reduce (although not eliminate) drying in the absence of polyethylene glycol (molecular weight of about 900–1600). Sorbitol is generally employed in water solution, typically about 50–80% by weight solution, preferably about 70%.

Amounts of water of at least about 25% by weight of a toothpaste typically about 25–50%, preferably about 25–40%, have been suggested in the prior art but have not been desirable since such high amounts of water permit ready drying of a toothpaste, perhaps due to evaporation, particularly when sorbitol is present as humectant.

The liquid phase of the toothpaste vehicle, that is humectant, water and additive to reduce drying comprises about 45–85% by weight of the toothpaste, preferably about 60–75%.

The gelling agent may be the natural and synthetic gums and gumlike material, e.g., Irish moss, gum tragacanth, methyl cellulose, hydroxyethyl cellulose, sodium carboxymethyl cellulose, and starch, usually in amount about 0.5–10% by weight and preferably about 0.5–5% of the formulation. The preferred gelling agents are sodium carboxymethyl cellulose and hydroxyethyl cellulose.

Further gelling agents which may be employed are hydrophilic carboxyvinyl polymers such as those sold under the trademark Carbopol 934 and 940 and synthetic silicated clays such as those sold under the trademark Laponite CP and SP.

In addition to the gelling agent as the solid portion of the toothpaste vehicle, a thickener, such as a thinly divided synthetic colloidal silica sold under the trademarks Cab-o-Sil, Aerosil D200 and Syloid 244 and 266, may be present in amount of about 1–5% by weight.

There is distributed in the toothpaste vehicle a dentally acceptable water-insoluble polishing material typically in amount of about 15–50% by weight most preferably about 25–45%. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, alumina, hydrated alumina, aluminium silicate, zirconium silicate, silica, sodium aluminosilicate, bentonite, and mixtures thereof. Preferred polishing materials include complex amorphorus sodium aluminosilicate, anhydrous alumina, calcium carbonate and dicalcium phosphate. The polishing materials may be used in admixture.

In the present invention about 5–20% by weight, preferably about 6–8%, of polyethylene glycol having an average molecular weight between about 900 and 1600 is effective in reducing or preventing formula drying which causes undesirable plugging of the cap of a toothpaste tube in which such toothpastes are commonly placed. The preferred average molecular weight range is about 900–1050.

Polyethylene glycol is commercially available from Union Carbide Chemical Company under the trademark Carbowax and also from Fabwerke Hoechst A. G. Lankro Chemicals Ltd. and Shell Chemicals Ltd.

Polyethylene glycol of average molecular weight below about 900, such as of average molecular weight of about 380–420 or about 570–630 have kinematic viscosities in aqueous solutions such that they are quite liquid. In fact such grades of polyethylene glycol have been suggested as humectant liquid phase additives for toothpastes. The kinematic viscosities of aqueous solutions of polyethylene glycol having an average molecular weight of above about 900, such as about average molecular weight of about 900–1050 and about 1300–1600, are such that they are measurably thicker than Carbowax 400 or 600. However they are easily soluble in the liquid phase of a toothpaste. Drying and plugging can also be reduced when polyethylene glycol of average molecular weight greater than about 1600, such as about 3000–4800. However, other side effects such as phase separation can occur when such higher molecular weight materials are employed.

Organic surface-active agents are used in the compositions of the present invention to achieve increased prophylactic action, assist in achieving thorough and complete dispersion of the instant compositions throughout the oral cavity, and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. Suitable such detergents are water-soluble salts of higher fatty acid monoglyceride monosulphates, such as sodium lauryl sulphate, alkyl aryl sulphonates, such as sodium dodecyl benzene sulphonate, higher alkyl sulphoacetates, higher fatty acid ester of 1,2 dihydroxy propane sulphonates, and the substantially saturated higher aliphatic acyl amides of lower aliphatic amino carboxylic acid compounds, such as those having 12 to 16 carbons in the fatty acid, alkyl or acyl groups and the like. Examples of the last mentioned amides are N-lauroyl sarcosine, and the sodium, potassium and ethanolamine salts of N-lauroyl, N-myristoyl or N-palmitoyl sarcosine which should be substantially free from soap or similar higher fatty acid material which tends to substantially reduce the effect of these compounds. The use of these sarcosinate compounds in dentifrice compositions of the present invention is particularly advantageous since these materials exhibit a prolonged and marked effect in the inhibition of acid formation in the oral cavity due to carbohydrates breakdown in addition to exerting some reduction in the solubility of tooth enamel in acid solutions.

Other particularly suitable surface-active materials include nonionic agents such as condensates of sorbitan monostearate with approximately 60 moles of ethylene oxide, condensates of ethylene oxide with propylene oxide condensates of propylene glycol (available under the trademark ("Pluronics") and amphoteric agents such as quaternized imidazol derivatives which are available under the trademark "Miranol" such as Miranol C2M. Cationic surface-active germicides and antibacterial compounds such as diisobutylphenoxyethoxyethyl dimethyl benzyl ammonium chloride, benzyl dimethyl stearyl ammonium chloride, tertiary amines having one fatty alkyl group (of from 12 to 18 carbon atoms) and two (poly) oxyethylene groups attached to the nitrogen (typically containing a total of from about 2 to 50 ethanoxy groups per molecule) and salts thereof with acids and compounds of the structure

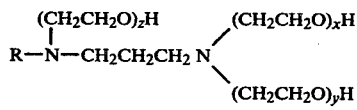

where R is a fatty alkyl group containing from about 12 to 18 carbon atoms, and x, y, and z total 3 or higher, as well as salts thereof with mineral or organic acids, may also be used. It is preferred to use from about 0.05 to 5% by weight of the foregoing surface-active materials in the instant oral preparations.

A fluorine-providing compound may be present in the toothpaste. This compound may be slightly soluble in water or may be fully water-soluble. It is characterised by its ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, a copper fluoride such as cuprous fluoride, zinc fluoride, a tin fluoride such as stannous fluoride or stannous chlorofluoride, barium fluoride, sodium fluorosilicate, ammonium fluorosilicate, sodium fluorozirconate, sodium monofluorophosphate, aluminium mono and difluorophosphate. Alkali metal and tin fluorides, such as sodium and stannous fluorides, sodium monofluorophosphate and mixtures thereof, are preferred. A mixture of sodium fluoride and sodium monofluorophosphate is particularly desirable. In the toothpaste an amount of fluorine-providing compound which releases a maximum of about 1% by weight of the toothpaste is satisfactory. Any suitable minimum amount of such compound may be used, but it is preferable to employ sufficient compound to release from about 0.005% to 1%, and preferably about 0.1% of fluoride ion. Typically, in the cases of alkali metal fluorides and stannous fluoride, this component is present in an amount up to 2% by weight, based on the weight of the toothpaste, and preferably in the range of from 0.05% to 1%. In the case of sodium monofluorophosphate, the compound may be present in an amount up to 7.6% by weight, more typically 0.76%. When present in mixture the ratio of sodium monofluorophosphate to sodium fluoride is desirably about 1:1 to 3:1 based on fluorine provided by each.

Any suitable flavouring or sweetening material may also be employed. Examples of suitable flavouring constituents are flavouring oils, e.g., oils of spearmint, peppermint, wintergreen, sassafras, clove, sage, eucalyptus, marjoram, cinnamon, lemon and orange, and methyl salicylate. Suitable sweetening agents include sucrose, lactose, maltose, sorbitol, sodium cyclamate, perillartine, and sodium saccharin. Suitably, flavouring and sweetening agents may together comprise from 0.01% to 5% or more of the preparations.

Various other materials may be incorporated in the oral preparations of this invention. Examples thereof are colouring or whitening agents, preservatives, silicones, chlorophyll compounds, ammoniated materials such as urea, diammoniumphosphate and mixtures thereof, and other constituents. These adjuvants are incorporated in the instant compositions in amounts which do not substantially adversely affect the properties and characteristics desired and are selected and used in proper amount depending upon the particular type of preparation involved.

The dental cream typically has a pH (determined directly on the cream) of about 4 to 10.5, preferably about 6–10. If desired, the pH may be adjusted with an acidic material, such as benzoic or citric acid, or an alkaline material, such as sodium hydroxide, to achieve a particular value, Buffering agents, e.g., phosphate buffers, may be used.

The dental cream may be prepared by adding humectant to water and blending therewith the gelling agent and thereafter the polishing material.

In evaluating toothpastes of the present invention, viscosity may be determined with the Universal Testing Instrument (Table Model) manufactured by Instron Ltd., High Wycombe, England. Viscosity comparisons can also be determined with an extensive rheometer.

The following specific example is further illustrative of the nature of the present invention but it is understood that the invention is not limited thereto. The composition are prepared in the usual manner and all amounts and proportions are by weight unless otherwise specified.

EXAMPLE

The following toothpastes are prepared, deaerated and placed in unlined aluminium toothpaste tubes which are left uncapped.

|  | PARTS | | | | |
| --- | --- | --- | --- | --- | --- |
|  | A | B | C | D | E |
| Sorbitol (70% solution) | 20.00 | 20.00 | 20.00 | 23.00 | 23.00 |
| Sodium carboxymethyl cellulose | 1.10 | 1.10 | 1.10 | 1.10 | 1.10 |
| Sodium saccharin | 0.18 | 0.18 | 0.18 | 0.18 | 0.18 |
| Titanium dioxide | 0.40 | 0.40 | 0.40 | — | — |
| Sodium monofluorophosphate | 0.82 | 0.82 | 0.82 | — | — |
| Sodium aluminosilicate (about 7% alumina) | 20.00 | 20.00 | 20.00 | — | — |
| Anhydrous alumina | 10.00 | 10.00 | 10.00 | — | — |
| Calcium carbonate | — | — | — | 42.00 | 42.00 |
| Polyethylene glycol - M.wt. 950-1050 (Hoechst) | — | 6.00 | — | — | 6.00 |
| Polyethylene glycol - M.wt. 1400-1600 (Hoechst) | — | — | 6.00 | — | — |
| Sodium lauryl sulphate | 1.50 | 1.50 | 1.50 | 1.50 | 1.50 |
| Sodium silicate (33% solution) | — | — | — | 0.20 | 0.20 |
| Flavour | 1.00 | 1.00 | 1.00 | 1.00 | 1.00 |
| Water | 45.00 | 39.00 | 39.00 | 31.12 | 25.12 |

Toothpastes A and D quickly dry and hard plugs in the necks of the tubes form within 7 hours of being left opened and extrusion is difficult, while with toothpastes B and C at most after 24 hours of being left opened only soft waxy plugs form and extrusions remain easy and with toothpaste E no plug forms at all.

Although this invention has been described with regard to specific example, it will be apparent to one skilled in the art that various modifications may be made thereto which fall within its scope.

We claim:

1. A toothpaste suitable for being tubed and capped which when left uncapped has reduced hard plug formation which if formed would make it difficult to extrude the toothpaste from a tube comprising about 15-50% by weight of a dentally acceptable water-insoluble polishing material distributed in a vehicle, said vehicle containing about 45-85% by weight of a liquid phase which consists essentially of humectant including the presence of sorbitol, which sorbitol is present as sorbitol solution in amount of about 15-35% by weight of said toothpaste, and about 25-50% by weight of non-solution water, and about 5-20% of an agent which reduces drying and hard plug formation and a solid phase including about 0.5-10% by weight of gelling agent, wherein there is present as said agent of the liquid phase which reduces drying and hard plug formation polyethylene glycol having an average weight between about 900 and 1600.

2. A toothpaste claimed in claim 1 wherein said sorbitol solution is present in an amount of about 15-35% by weight.

3. A toothpaste claimed in claim 2 wherein said sorbitol solution is present in an amount of about 20-25% by weight.

4. A toothpaste claimed in claim 1 wherein said non-solution water is present in an amount of about 25-50% by weight.

5. A toothpaste claimed in claim 4 wherein said non-solution water is present in an amount of about 25-40% by weight.

6. A toothpaste claimed in claim 1 wherein said liquid phase is present in amount of about 60-75% by weight and comprises about 15-35% by weight of said sorbitol solution, about 25-50% by weight of non-solution water and about 6-8% by weight of said polyethylene glycol.

7. The toothpaste claimed in claim 1 wherein said polishing agent is sodium aluminosilicate.

8. The toothpaste claimed in claim 1 wherein said polishing agent is calcium carbonate.

9. The toothpaste claimed in claim 1 wherein said polyethylene glycol has an average molecular weight of about 900-1050.

10. The toothpaste claimed in claim 1 wherein said polyethylene glycol has an average molecular weight of about 1300-1600.

* * * * *